(12) United States Patent
Hanna et al.

(10) Patent No.: US 6,440,337 B1
(45) Date of Patent: Aug. 27, 2002

(54) METHOD AND APPARATUS FOR THE FORMATION OF PARTICLES

(75) Inventors: Mazen Hanna, Bradford; Peter York, West Yorkshire, both of (GB)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

(21) Appl. No.: 09/380,025

(22) PCT Filed: Feb. 20, 1998

(86) PCT No.: PCT/GB98/00538

§ 371 (c)(1),
(2), (4) Date: Dec. 16, 1999

(87) PCT Pub. No.: WO98/36825

PCT Pub. Date: Aug. 27, 1998

(30) Foreign Application Priority Data

Feb. 21, 1997 (GB) .............................................. 9703673

(51) Int. Cl.[7] .................................................. B29B 9/00
(52) U.S. Cl. ................................ 264/11; 264/12; 425/7
(58) Field of Search ......................... 264/11, 12; 425/6, 425/7

(56) References Cited

FOREIGN PATENT DOCUMENTS

| GB | 473471 | 10/1937 |
|----|--------|---------|
| GB | 621785 | 8/1945 |
| WO | WO 89/05196 | 6/1989 |
| WO | WO 95/01221 | 1/1995 |
| WO | WO 96/00610 | 1/1996 |

*Primary Examiner*—Allan R. Kuhns
(74) *Attorney, Agent, or Firm*—Michael J. Rafa; Felissa H. Cagan

(57) ABSTRACT

The invention provides a method and apparatus for forming particles of a substance, comprising (a) introducing into a particle formation chamber, the temperature and pressure in which are controlled, a first supercritical fluid (SCF) and a solution or suspension of the substance in a vehicle; (b) simultaneously introducing an impinging flow of a second supercritical fluid (SCF), at an angle to, and directed at, the direction of flow of the first supercritical fluid, so as to increase the amount of kinetic energy transferred to the solution or suspension; and (c) using either or both of the first and the second supercritical fluids to disperse the solution or suspension, and to extract the vehicle from it, substantially simultaneously and substantially immediately on introduction of the fluids into the particle chamber.

33 Claims, 12 Drawing Sheets

METHOD AND APPARATUS FOR THE FORMATION OF PARTICLES

FIELD OF THE INVENTION

Figure 1:
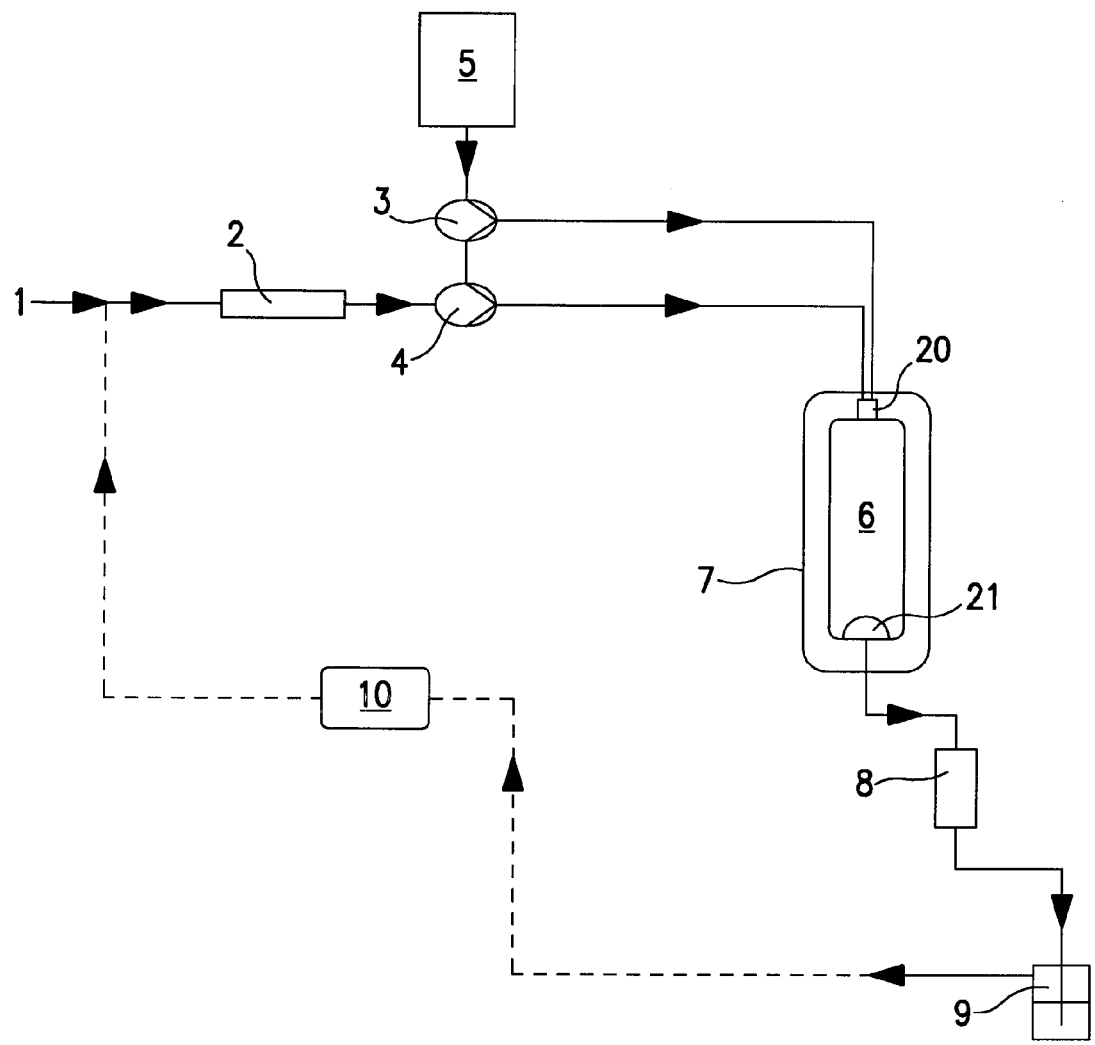

This invention relates to the controlled formation of particulate products using supercritical fluids. It provides a method and apparatus for the formation of substances in particulate form, and also the particulate product of the method.

BACKGROUND TO THE INVENTION

The invention relates generally to the formation of particles of a substance of interest, from a solution or suspension of that substance in an appropriate vehicle, using a supercritical fluid to extract the vehicle and hence cause precipitation of a particulate product.

More particularly, it concerns modifications to an existing technique for particle formation using supercritical fluids, described in WO-95/01221 and (in a modified form) in WO-96/00610. The technique is known as "SEDS" (Solution Enhanced Dispersion by Supercritical Fluids). Its essence is that a solution or suspension of a substance of interest, in an appropriate vehicle, is co-introduced into a particle formation vessel with a supercritical fluid, in such a way that dispersion and extraction of the vehicle occur substantially simultaneously by the action of the supercritical fluid, and substantially immediately on introduction of the fluids into the vessel. The pressure and temperature inside the particle formation vessel are carefully controlled during this process.

SEDS allows a high degree of control over conditions such as pressure, temperature and fluid flow rates, and over the physical dispersion of the solution/suspension, at the exact point where particle formation occurs (ie, at the point where the vehicle is extracted into the supercritical fluid). It therefore allows excellent control over the size, shape and other physical and/or chemical properties of the particles formed.

The present invention builds on this existing technology. It provides a modification to the SEDS technique, which can lead to greatly improved control over the characteristics of the particulate product.

Accordingly, most of the technical features of SEDS, as disclosed in WO-95/01221 and WO-96/00610, apply also to the present invention. The technical information contained in the earlier publications, as to the execution of SEDS, is also applicable when carrying out the present invention and as such, WO-95/01221 and WO-96/00610 are intended to be read together with the present application.

STATEMENTS OF THE INVENTION

According to a first aspect of the present invention there is provided a method for forming particles of a substance, the method comprising (a) introducing into a particle formation chamber, the temperature and pressure in which are controlled, a first supercritical fluid and a solution or suspension of the substance in a vehicle; (b) simultaneously introducing, into the particle formation chamber, an impinging flow of a second supercritical fluid, at an angle to, and directed at, the direction of flow of the first supercritical fluid; and (c) using either or both of the first and second supercritical fluids to disperse the solution or suspension, and to extract the vehicle from it, substantially simultaneously and substantially immediately on introduction of the fluids into the particle formation chamber.

This method retains all the advantages of the SEDS technique. The simultaneous introduction of the solution or suspension and the supercritical fluids, into a chamber inside which pressure and temperature are controlled, allows a high degree of control of operating parameters at the exact point when the fluids come into contact with one another and therefore at the point of actual particle formation. Importantly, the mechanical action of the supercritical fluids is used to disperse the solution/suspension, whilst at the same time they extract the vehicle from it—because of this, controlling the relative flow rates of the fluids allows accurate control over the size of the fluid elements (eg, droplets) formed on dispersion of the solution/suspension, and hence of the particles formed substantially simultaneously by extraction of the vehicle into the supercritical fluid(s).

However, the method of the present invention allows for greatly improved dispersion of the solution or suspension of the substance of interest, by the additional impinging (preferably counter-current) flow of the second supercritical fluid. This improved dispersion can be attributed to enhanced physical contact between the solution/suspension and the (usually relatively high velocity and therefore also high kinetic energy) supercritical fluids, hence effecting the formation of very fine particles with an extremely narrow size distribution. The two supercritical fluid flows, directed at one another and usually in substantially opposite directions, each transfer their kinetic energy to the solution or suspension, serving to break it up into individual fluid elements; the size and size distribution of these elements can be very closely controlled by adjusting the flow rates of the various fluids and other working conditions such as the temperature and pressure inside the particle formation chamber. The solution/suspension can be subjected to a very high degree of dispersion due to the high overall supercritical fluid velocity (ie, high overall kinetic energy), and its efficient dispersion, at substantially the same time as the vehicle is extracted from it, in turn can provide a high degree of uniformity in the particles formed.

A further advantage of using two supercritical fluid flows, and hence introducing a higher level of kinetic energy into the solution/suspension at or near the point of particle formation, is that particles formed from the solution or suspension can be forced rapidly away from the point of particle formation and hence apparatus blockages (which might otherwise occur in the inlet means used to introduce the fluids into the particle formation chamber) can be reduced or even avoided. The supercritical fluids thus serve to disperse the solution or suspension, to extract the vehicle from it and to remove particulate products from the region of particle formation. The high velocities of the supercritical fluids facilitate quick removal of the particles, ensuring that they cannot reunite with fluid elements, aggregate with one another or otherwise clog up the region of particle formation.

The directions of flow of the first supercritical fluid and the solution or suspension may be substantially parallel, for instance coaxial, as described in WO-95/01221 and WO-96/00610. However, the solution or suspension may in the present invention be introduced at an angle (eg, of up to 90°) to the flow of the first supercritical fluid, so long as it is then dispersed by the supercritical fluid(s) immediately it comes into contact with them. Generally speaking, the directions of flow of all the fluids should be chosen so as to maximise the amount of physical contact between them in the region of particle formation; this in turn serves to maximise the amount of kinetic energy transferred from the supercritical fluids to the solution/suspension and to the particulate products, thus improving dispersion and more efficiently removing particles from areas of potential blockage. The use of two supercritical fluid flows together improves these processes yet further and ensures better control over the mechanism of particle formation.

According to a second aspect, the present invention provides apparatus suitable for carrying out the above described method. The apparatus comprises a particle formation chamber; means for controlling the temperature in the chamber at a desired level; means for controlling the pressure in the chamber at a desired level; first fluid inlet means for the introduction into the chamber of a first supercritical fluid and a solution or suspension of the substance of interest in a vehicle; and second fluid inlet means for introducing simultaneously an impinging flow of a second supercritical fluid, at an angle to, and directed at, the direction of flow of the first supercritical fluid, the apparatus being such as to allow dispersion of the solution or suspension, and extraction of the vehicle, to occur substantially simultaneously and substantially immediately on introduction of the fluids into the particle formation chamber, by the action of either or both of the two supercritical fluids.

Again, the first fluid inlet means preferably allows the co-introduction of the first supercritical fluid and the solution or suspension, for instance in substantially parallel directions or even coaxially.

In both first and second aspects of the invention, the second supercritical fluid preferably flows in a direction substantially opposite to that of the first, ie, the angle at which it is directed at the first supercritical fluid flow is preferably about 180°. However, other impinging angles may be chosen, again the general idea being to maximise physical contact between the fluids in the region of particle formation. The first and second supercritical fluids will usually, although not necessarily, meet at or very close to the point of particle formation, ie, the point at which they contact the solution or suspension.

In the present invention, and the current description of it, the term "supercritical fluid" means a fluid substantially at or above its critical pressure ($P_c$) and critical temperature ($T_c$) simultaneously. In practice, the pressure of the fluid is likely to be in the range $(1.01-7.0)P_c$, and its temperature in the range $(1.01-4.0)T_c$.

The term "vehicle" means a fluid which is able to carry a solid or solids in solution or suspension. A vehicle may be composed of one or more component fluids. The vehicle used in the present invention should he substantially soluble in the chosen supercritical fluids, to allow its extraction at the point of particle formation.

The term "supercritical solution", as used herein, means one or more supercritical fluids together with one or more vehicles which it or they have extracted and dissolved. The solution will usually, although not necessarily, itself be in the supercritical state, at least within the particle formation chamber.

The verb "disperse", unless the context clearly requires otherwise, refers to the formation of droplets, or of other analogous fluid elements, of the solution or suspension and/or of the vehicle.

The substance to which the method of the invention is applied may be any substance which needs to be produced in particulate form. It may be a substance for use in or as a pharmaceutical. However, the particulate product may also be a product of use in the ceramics, explosives or photographic industries; a foodstuff; a dye; a coating; etc. In each case, the principle behind the method of the invention remains the same; the technician need only adjust operating conditions in order to effect proper control over the characteristics of the particles being formed.

The substance may be in a single or multi-component form—it could for instance comprise an intimate mixture of two materials, or one material in a matrix of another, or one material coated onto a substrate of another, or other similar mixtures. The particulate product, formed from the substance using the method of the invention, may also be in a multi-component form—such products may be made from solutions or suspensions containing only single component starting materials, provided the solutions/suspensions are introduced with the supercritical fluids in the correct manner (more than one solution/suspension may be introduced into the particle formation chamber with the supercritical fluids). The particulate product may also be a substance formed from an in situ reaction (ie, immediately prior to, or on, dispersion by the supercritical fluid(s)) between two or more reactant substances, each carried by an appropriate vehicle. Such modifications to the SEDS process, involving the use of in situ reactions and/or more than one solution or suspension of a substance of interest, are described in WO-95/01221 and WO-96/00610, and can also be applied when carrying out the present invention.

Each of the first and second supercritical fluids may be any suitable supercritical fluid, for instance supercritical carbon dioxide, nitrogen, nitrous oxide, sulphur hexafluoride, xenon, ethylene, chlorotrifluoromethane, ethane, trifluoromethane or mixtures thereof. A particularly preferred supercritical fluid is supercritical carbon dioxide, due to its relatively low cost, toxicity, flammability and critical temperature.

The second and first supercritical fluids are preferably, but not necessarily, the same; again, conveniently both are supercritical carbon dioxide.

Either or both of the supercritical fluids may optionally contain one or more modifiers, for example methanol, ethanol, isopropanol, acetone or water. When used, a modifier preferably constitutes not more than 20%, and more preferably between 1% and 10%, mole fraction of the supercritical fluid. The term "modifier" is itself well known to those skilled in the art. A modifier (or co-solvent) may be described as a chemical which, when added to a supercritical fluid, changes the intrinsic properties of the fluid in or around its critical point.

The vehicle may be any appropriate fluid which either dissolves or suspends the substance of interest and is itself substantially soluble in the chosen supercritical fluids. The choice of vehicle in any particular case will depend on the nature of the substance, on the supercritical fluids and on other practical criteria including those governing the desired end product. The term "vehicle" encompasses a mixture of two or more fluids which together have the necessary characteristics vis-a-vis the substance of interest and the supercritical fluids.

The choice of a suitable combination of supercritical fluids, modifier (where desired) and vehicle for any desired product will be well within the capabilities of a person of ordinary skill in the art.

The relative flow rates of the fluids introduced into the particle formation chamber may be used to control the size, size distribution and other characteristics of the particles formed. Each fluid flow rate may be separately adjusted. Preferably, the flow rates of the two supercritical fluids are much higher than that of the solution or suspension.

Typically, the ratio of the solution/suspension flow rate to each supercritical fluid flow rate will be between 0.001 and 0.2, preferably between 0.001 and 0.1, more preferably between 0.01 and 0.07. However, the fluid flow rates chosen in any particular case will depend entirely on the substance of interest and the types of fluids being used.

The flow rates of the supercritical fluids, relative to that of the solution/suspension, are particularly important because the supercritical fluids act to disperse the solution/suspension and to remove particles from the region of particle formation. Their flow rates therefore affect the size of the fluid elements caused by the dispersion, and hence of the particles formed by extracting the vehicle from those fluid elements. They also help to avoid blockages in the particle formation apparatus.

Through the pressure and temperature control in the particle formation chamber (and control of the fluid flow rates), supercritical conditions may be maintained in the chamber at all times. The flow rates of the supercritical fluids relative to that of the solution or suspension, and the pressures and temperatures of the fluids, should be sufficient to allow the supercritical fluids to accommodate the vehicle (generally, the vehicle will represent no more than around 5% mole fraction of the supercritical fluids), so that the vehicle can be extracted from the solution/suspension to cause particle formation. Careful selection of such operating conditions can ensure the existence of only a single phase during most of the particle formation process, in the solution containing the supercritical fluids and the extracted vehicle. This in turn allows improved control over particle characteristics and substantially eliminates the risk of residual vehicle in the particulate product.

The fluids are preferably introduced into the particle formation chamber through fluid inlet means of the type described below in connection with the apparatus of the invention. Ideally, fluids should be made to flow in a smooth, continuous and preferably substantially pulse-less manner. This helps prevent draw-back of fluids into the inlet means, which could lead to particle precipitation in undesirable locations and blocking of apparatus.

The temperature in the particle formation chamber may be maintained at a desired level (preferably ±0.1° C.) by means of a heating jacket or an oven. The pressure in the chamber is conveniently maintained at a desired level (preferably ±2 bar) by means of a back-pressure regulator.

The precise temperatures and pressures used will depend upon the choice of supercritical fluids and whether or not modifiers are present. These conditions, together with the flow rates of the fluids, and the concentration of the substance in the vehicle, are the main variables which may be adjusted to control parameters such as size, size distribution, shape and crystalline form in the particulate product.

The method of the invention preferably additionally involves collecting the particles following their formation, more preferably in the particle formation chamber itself. The method may also involve recovering the solution formed on extraction of the vehicle into the supercritical fluid(s), separating the components of the solution and recycling one or more of those components for future use. In particular, either or both of the supercritical fluids may be removed, purified and recycled.

The method is preferably carried out in a substantially continuous, as opposed to batch-wise, manner. This means that the formation and collection of particles, and/or the recovery and recycling of fluids, are preferably carried out continuously.

In apparatus according to the second aspect of the invention, the first and second fluid inlet means preferably comprise first and second nozzles respectively The first fluid inlet means may in fact comprise two nozzles, one for introduction of the first supercritical fluid and one for introduction of the solution or suspension, arranged at an appropriate angle relative to one another. The first and second fluid inlet means may both form part of a single fluid inlet assembly usable to introduce all fluids into the particle formation chamber in the appropriate manner.

A preferred fluid inlet assembly comprises two main components:

a) a first, "primary" nozzle having two or more concentric passages, through which may be introduced a flow of the first supercritical fluid and a flow of the solution or suspension of the substance of interest; and b) a second, "secondary" nozzle having at least one passage directed at an angle to the primary nozzle passages, through which secondary nozzle passage a flow of the second supercritical fluid may be introduced, the outlets of the primary and secondary nozzle passages being positioned so as to allow supercritical fluid flowing through the secondary nozzle to impinge upon supercritical fluid flowing through the primary nozzle.

Preferably, the secondary nozzle passage is coaxial with the primary nozzle passages but points in the opposite direction, so that the outlet end of the secondary nozzle passage faces the outlet ends of the primary nozzle passages.

The primary nozzle passages may be of the type which allow "pre-filming" or "sheathing" of at least one of the fluids to occur, immediately prior to its contact with the other fluid(s). Typically, the primary nozzle may be used to cause pre-filming of the solution or suspension, immediately prior to its dispersion by the supercritical fluid(s). This means that the dimensions of the primary nozzle passages, and the relative positions of their outlets, must be such that a fluid entering through one passage is formed, as it reaches the outlet of that passage, into a thin film or sheath by its contact with, say, the lip of an adjacent passage outlet. This film or sheath can then be stretched (destabilised, and ultimately dispersed into separate fluid elements, when it comes into contact with a stream of a high velocity fluid in another nozzle passage and/or with an impinging stream from the secondary nozzle. Clearly, the thickness of the film or sheath, and hence the size of the fluid elements formed on dispersion, will depend on the relative flow rates of the fluids, and also on the nozzle geometry.

The outlets of the primary nozzle passages should be reasonably close to that of the secondary nozzle passage, again so as to maximise kinetic energy transfer between the second supercritical fluid and the solution/suspension. The actual distance and angle between them will depend, for instance, on the size, type and shape of particles it is desired to form, on the nature of the substance and the fluids, on the fluid flow rates to be used, on manufacturing constraints, etc.

For the at least two primary nozzle passages, the outlet of an inner passage may occur either upstream or downstream of that of one or more of the surrounding outer passage(s) or at virtually the same location. In the first case, contact between a solution/suspension passing through the inner passage and a first supercritical fluid passing through a surrounding passage occurs inside the primary nozzle and before the two together contact the second supercritical fluid. Accordingly, a degree of dispersion and extraction can occur before further dispersion by the second supercritical fluid. Such an inlet assembly may also for example be used in carrying out in situ reactions, for instance between one component carried in the vehicle and another in the first supercritical fluid, or between two components carried in two separate vehicles down two out of three primary nozzle passages, which reactions take place just within the primary nozzle, immediately prior to extraction of the vehicle or vehicles and particle formation. It could further be used, for instance, in the preparation of coated particles or particles in which one component is impregnated in a matrix of another.

(An alternative way of using this "first case" primary nozzle would be to introduce the first supercritical fluid through the inner passage and the solution/suspension through a surrounding passage. The solution/suspension would form a conical film surrounding the outlet of the inner passage, the surface of which film would be destabilised by the high velocity supercritical fluid emerging from the inner passage, leading ultimately to dispersion of the solution/suspension.)

In the second case scenario, both the first and the second supercritical fluids can together act to disperse a solution or suspension passing through the inner primary nozzle passage. This can increase the level of control over the particle characteristics and so is often one of the preferred arrangements. In this case, in situ reactions, coating, impregnation and other multi-component operations may still be carried out, by introducing further components through additional secondary nozzle passages. The secondary nozzle may itself, therefore, comprise two or more concentric passages, so that solutions or suspensions of substances of interest, as well as the second supercritical fluid, may be introduced at an angle to the first supercritical fluid flow. The same comments apply to the two or more secondary nozzle passages, as regards the positions of their outlets, and the desirability of the pre-filming approach, as to the primary nozzle passages.

The fluid inlet assembly typically comprises an intermediate chamber located between the primary and the secondary nozzle outlets, in which chamber the fluids may meet and interact. This chamber is preferably shaped to direct the fluids and/or particles formed from them, away from the point at which the fluids meet. Since particle formation typically occurs virtually at the nozzle outlets, the intermediate chamber itself forms part of the particle formation chamber. The intermediate chamber could, for instance, be directed at an angle (including perpendicular) to the primary and secondary nozzle passages, and in use may be downwardly directed so as to allow gravity to contribute (together with the relatively high overall velocity of the two supercritical fluid flows) to removal of particulate products from the nozzle outlet region. The size and shape of the intermediate chamber may be used in part to determine the characteristics of the particles formed, and again to contribute towards efficient particle removal and to minimise the risk of solution droplets uniting with the particles and causing agglomeration. To this end, the intermediate chamber should be so sized and shaped as to maximise fluid turbulence in or around the region of particle formation, which again enhances physical contact between the fluids and aids dispersion of the solution/suspension and removal of particulate products.

The nozzle passages may conveniently be made of stainless steel; other suitable materials include sapphire, high performance ceramics and high performance polymers. Other aspects of the design of the inlet assembly, for instance the diameters of the nozzle passages and their outlets, the positioning of the primary and secondary nozzles relative to one another, the number of passages in each nozzle and the uses to which they may be put, are as disclosed in WO-95/01221 and WO-96/00610 (although these documents refer to nozzles providing only one direction of flow, their teachings may apply equally to the primary or the secondary nozzle passages of use in the apparatus of the present invention).

When carrying out the method of the invention using such an inlet assembly, the fluid flow rates are preferably chosen so that the precipitated particles are caused to leave the inlet assembly virtually as soon as they are formed, so as to avoid blocking of the nozzle passage outlets. Again, the design of the intermediate chamber may be chosen so as to help in this, by creating the desired flow characteristics in the region of particle formation.

According to a third aspect, the present invention provides a fluid inlet assembly of the type described above.

The invention also provides, according to a fourth aspect, a particulate product formed using the method of the first aspect and/or the apparatus of the second.

BRIEF DESCRIPTION OF THE DRAWINGS

The invention will now be described, by way of example only, with reference to the accompanying illustrative drawings, in which:

FIG. 1 shows schematically apparatus for use in carrying out a method in accordance with the invention;

FIG. 2 is a cross-section through a fluid inlet assembly for introducing fluids into the particle formation chamber in the apparatus of FIG. 1;

FIGS. 3 and 4 are more detailed cross-sections showing the two nozzle outlets of the inlet assembly of FIG. 2;

FIG. 5 is a cross-section through the inlet assembly of FIG. 2, connected to other components for use as part of the apparatus of FIG. 1;

FIGS. 6–9 are schematic cross-sections through alternative inlet assemblies for use in the apparatus of FIG. 1;

FIGS. 10 and 11 are particle size distribution curves relating to Example 1 below;

FIGS. 12–15 are SEM micrographs of the products of Examples 1–4 respectively;

FIG. 16 is an SEM micrograph of an alternative: product made in Example 4; and FIGS. 17–19 are SEM micrographs of the products of Examples 5, 6 and 7 respectively.

DETAILED DESCRIPTION OF THE INVENTION

Referring firstly to FIG. 1, the apparatus shown includes a particle collection vessel 6. This is typically a standard reaction vessel, for instance of the type available from Keystone Scientific Inc, of an appropriate capacity for the particular use to which it is to be put. The temperature and pressure in the vessel may be maintained at a constant desired level, by means of an oven 7 and a back pressure regulator 8 respectively.

When used in accordance with the present invention, the system is initially pressurised and stable working conditions are met. A suitable gas, for example carbon dioxide, is fed from source 1 to a cooler 2 (to ensure liquification) and, via pump 4, to a fluid inlet assembly 20 communicating with the interior of the vessel 6. A solution of a substance of interest in a suitable vehicle is drawn from source 5 by a pump 3 and also fed to the vessel 6 via inlet assembly 20.

The inlet assembly 20 is shown only schematically in FIG. 2 and will be described in more detail below. It introduces the supercritical fluid formed in cooler 2 (in two oppositely-directed flows) and the solution from source 5, into the particle collection vessel in the manner required by the method of the invention. Particle formation occurs primarily in an intermediate chamber within the inlet assembly, and the particles formed fall into the vessel 6 where they are retained by collecting means 21. The resultant supercritical solution is fed to a back pressure regulator 8 and thence to a separation vessel 9, where it is allowed to expand, causing the supercritical fluid to separate as a gas from the liquid vehicle. The gas may then be fed to a tank 10 and returned to the cooler 2. The vehicle may also be collected for subsequent re-use. Means, not shown, may be provided to smooth the fluid flow pulses produced by the pumps 3 and 4.

When sufficient particle formation has occurred, the inlet assembly and the vessel 6 are flushed through with clean, dry supercritical fluid, so as to ensure removal of any residual vehicle. The vessel can then be de-pressurised and the particulate product removed.

During the particle formation process, the temperature and pressure within vessel 6 are maintained at a supercritical level, ie, a level which ensures that the solution formed on extraction of the vehicle into the supercritical fluid remains in a supercritical condition both during and after particle precipitation, or at least reaches a supercritical condition as soon as possible after particle formation.

The inlet assembly 20 may take the form shown in FIGS. 2–5, or alternatively that shown in any of FIGS. 6–9.

Figure 2:
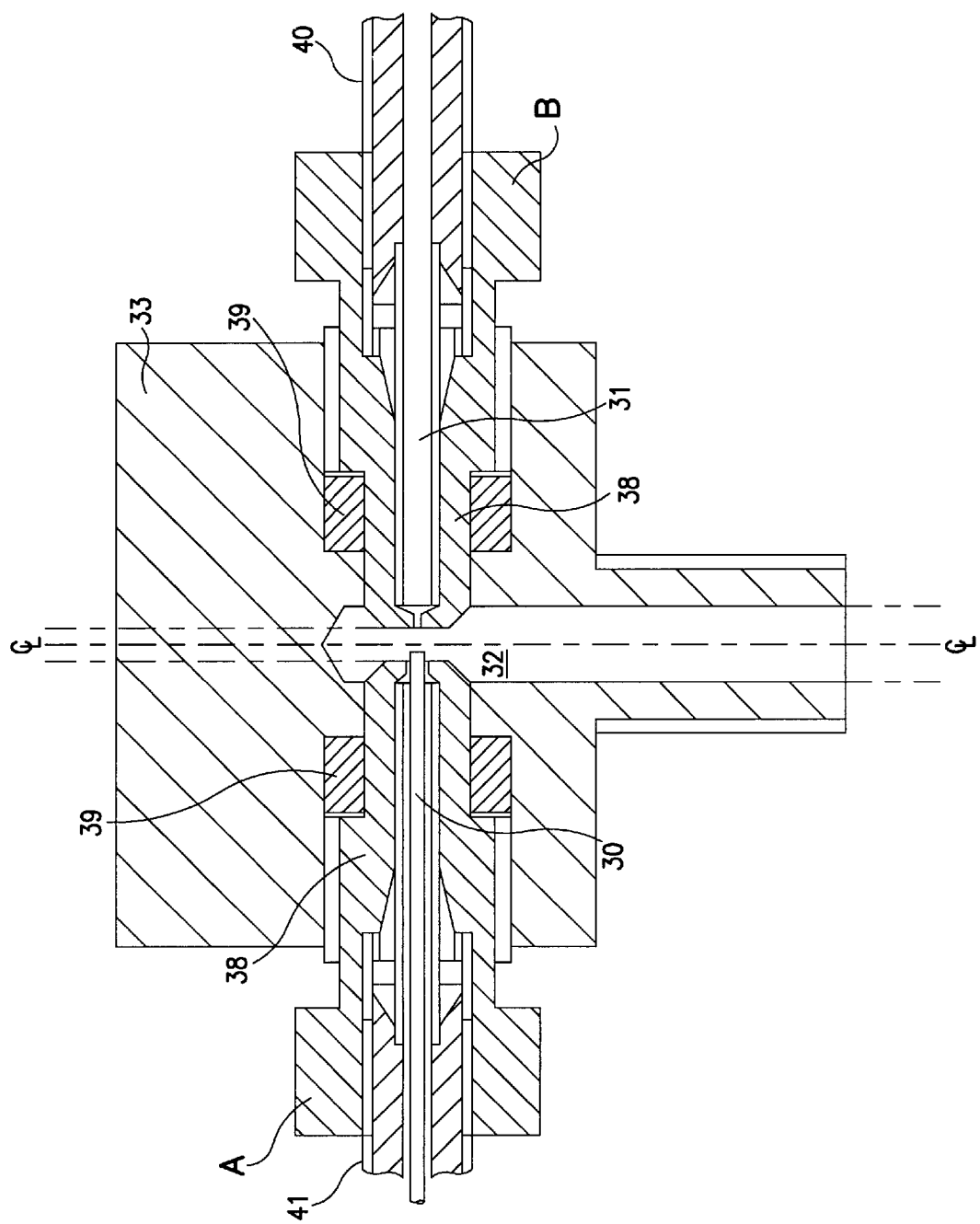

Referring now to FIG. 2, the inlet assembly illustrated comprises two oppositely directed inlet nozzles generally labelled 30 and 31. The outlets of these two nozzles terminate facing one another in the intermediate chamber 32, in which fluid mixing and particle formation occur during use of the apparatus. The outlet portions of the nozzles are housed in heating block 33, to allow temperature control at the nozzle outlets and within chamber 32.

Figure 3:
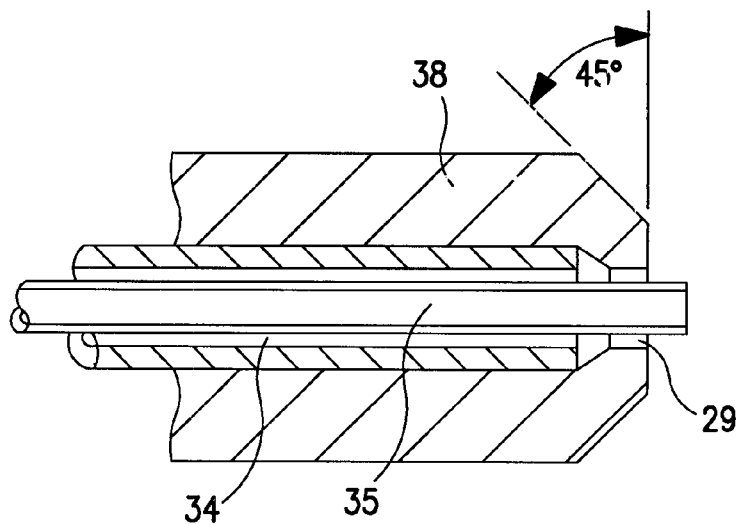
Figure 4:
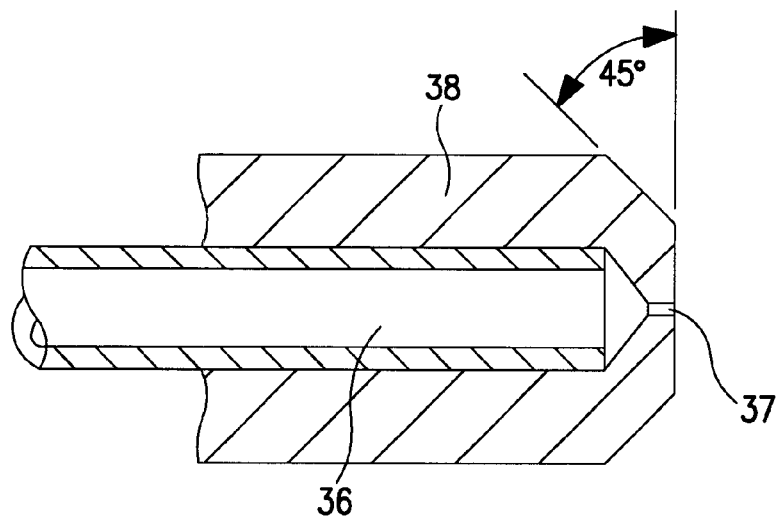

The "primary" nozzle 30 can be seen in more detail in FIG. 3. It comprises two concentric passages 34 and 35, of which the inner (35) terminates downstream of the outer. The outer passage 34 ends in a terminating passage section 29. The inlet assembly is arranged to allow introduction of two separate fluids into these two passages.

The protrusion of the inner passage beyond the outlet of the outer passage is advantageous because, in use, a solution or suspension emerging from the inner passage can be subjected, simultaneously, to the effects of two supercritical fluid flows, that through the outer primary nozzle passage 34 and also the oppositely directed flow through "secondary" nozzle 31. This ensures a more efficient dispersion of the solution/suspension, and helps to prevent clogging at the nozzle outlets as particle formation takes place.

The length of the protruding portion of the inner passage 35 may again be chosen according to requirements; it should be short enough for fluid contact and enhanced dispersion to occur in accordance with the method of the invention.

The secondary nozzle 31 (see FIG. 4) comprises only a single passage 36, with a narrower terminating passage section 37. The passages of both nozzles are made of 316 stainless steel, mounted in stainless steel mounting blocks 38.

Other components of the inlet assembly of FIG. 2 are shown in more detail in FIG. 5, and described below.

The dimensions of the nozzle passages should be chosen to suit the particular circumstances of their use, ie, to allow appropriate fluid flow rates, product yields and the like. In the inlet assembly illustrated in FIG. 2, primary nozzle 30 has an internal diameter of 0.35 mm for its inner passage 35 and an internal diameter of 0.75 mm for its outer passage 34. Inner passage 35 terminates 0.2 mm downstream of the outlet end of the terminating section 29 (length 0.5 mm) of outer passage 34. The internal diameter of the secondary nozzle passage 36 is 0.75 mm, with a terminating passage section 37 of internal diameter 0.15 mm and length 0.4 mm. The angle of taper at the outlet of the main passage 36 is 45°.

The mounting blocks 38 also have a 45° chamfer at the nozzle outlets, of about 0.9 mm depth. (Note that in practice, the upstream edges of these chamfered portions do not align exactly with the inner walls of the intermediate chamber 32, even though it may appear that way from FIG. 2.) It may be preferable to increase the chamfer depth, so that the tip of each block tapers almost to a point near its respective nozzle outlet—this may help to reduce build-up of particulate product at and between the nozzle outlets.

The chamber 32 needs to be shaped to allow for mixing of the fluids introduced through the nozzle passages, and dispersion of the solution or suspension of the substance of interest; this in turn allows the formation of a "cloud" of dispersed particles which can more easily be pushed away (by the action of the supercritical fluid flows) into a collection vessel, rather than remaining in chamber 32 to clog the nozzle outlets. The internal diameter of the chamber 32 shown in FIG. 2 is 3.5 mm; a preferred form of inlet assembly might well have a narrower intermediate chamber (to increase fluid turbulence), or a wider one (which can help to reduce blockage and can make cleaning and maintenance generally easier). An intermediate chamber of the same internal diameter as the collection vessel to which it is to be connected (eg, around 14 mm) may be preferred, and would allow a more efficient dispersion of fluids and particulate products. In this latter case, the inlet nozzles should protrude further into the intermediate chamber, to retain the desired spacing between their outlets.

The width of the gap between the nozzle outlets (in this case 1.2 mm, measured between opposing faces of the mounting blocks 38) must be chosen in any given case to prevent build-up of particulate product in the chamber 32; it will depend therefore on parameters such as the fluid flow rates being used and the nozzle geometry. In particular, it should be chosen so as to achieve the maximum possible turbulence between the incoming fluids (and hence efficient fluid mixing), whilst minimising the risk of blockage at the nozzle outlets. Typically, the width of the gap may be between approximately 0.4 mm and 2.5 mm, more preferably between approximately 1 mm and 2 mm. Measured in another way, it may be between approximately two and twelve times the internal diameter of the nozzle passage outlets.

It is to be understood that dimensions quoted for the apparatus of FIG. 2 (intended for particle formation on a laboratory scale) may not necessarily be suitable in the large-scale production of particulate products, such as in industry. However, the skilled person will be able to modify such parameters to suit a given set of operating conditions, without the exercise of inventive skill.

FIG. 5 shows in more detail the components of, and used with, the inlet assembly of FIGS. 2–4. The two oppositely-directed nozzles 30 and 31, in their mounting blocks 38, are encased it heating block 33. Both nozzle mounting block s carry PEEK (poly ether-ether ketone) seals 39. The inlet of secondary nozzle 31 is connected to a standard inlet component 40 (Swagelock (trade mark) ¹⁄₁₆ inch stainless steel male union), through which a flow of supercritical fluid may be introduced into the chamber 32, in a direction opposite to that of fluids entering through the primary nozzle 30.

The inlet of nozzle 30 is connected to a standard Swagelock ¹⁄₁₆ inch stainless steel T-connector 41, which in turn is connected to a standard female inlet component 42 (Valco (trade mark) 2-2997 stainless steel female union). This arrangement allows the introduction of two separate fluids into nozzle 30, one (typically a supercritical fluid) directly into the T-connector 41 and thence into outer passage 34 of the nozzle, and one (typically a solution or suspension of a substance of interest) through the inlet component 42 into the inner nozzle passage 35.

The lower, outlet, end of chamber 32 is connected to the top of a Keystone (trade mark) high pressure vessel 43, of 25 mm external diameter, 14 mm internal diameter and 50 ml capacity. The connection is made via an end fitting member 44, PEEK collar seal 45 and PEEK vessel seal 46 (all also Keystone).

Components 47 are Swagelock ¹⁄₁₆ inch stainless steel ferrules; component 48 is an Alltech (trade mark) universal ¹⁄₁₆ inch stainless steel ferrule. Component 49 is a custom-made PEEK ferrule of 0.65 mm internal diameter.

When this inlet assembly is used in a method according to the invention, fluids are introduced into nozzles 30 and 31 in the manner described above, at appropriate flow rates, so as to meet in the chamber 32 at the nozzle outlets. Here, a number of things take place virtually simultaneously—the two supercritical fluid flows (usually at high flow rates relative to that of the solution/suspension of the substance of interest) disperse the solution/suspension into separate fluid elements (eg, droplets). The supercritical fluids at the same time extract the vehicle from the solution/suspension, causing precipitation of fine particles from the dispersed fluid elements. These particles fall downwardly through chamber 32, mainly under the influence of the incoming fluids and partly under the influence of gravity, into the high pressure collecting vessel 43.

It should be noted that both chamber 32 and vessel 43 serve together as a "particle formation chamber".

Turning now to FIGS. 6–9, alternative forms of fluid inlet assembly, again for use in a method according to the present invention, are illustrated. That in FIG. 6 has a primary nozzle comprising two concentric passages 50 and 51, of which the inner passage, 51 terminates upstream of (inside) outer passage 50. It also has a secondary nozzle comprising passage 52, coaxial with but facing the opposite direction to the primary nozzle passages, and an intermediate chamber 53 through which fluids and precipitated particles may be discharged. Typically, the nozzles are used to introduce into the chamber 53 two counter-current flows of supercritical fluid, through passages 50 and 52, and a solution or suspension of a substance of interest in a vehicle, through inner primary passage 51. Thus, in use, the solution or suspension initially contacts the first flow of supercritical fluid inside passage 50, and immediately thereafter contacts the second, counter-current, flow of supercritical fluid from passage 52. Both flows of supercritical fluid serve to disperse the solution or suspension, to extract the vehicle from it and to remove the particulate product.

Additional reactants may be carried in the supercritical fluid flowing through outer primary passage 50, to allow for in situ reactions with the substance(s) carried in the solution/suspension flowing through inner passage 51.

Alternatively, the FIG. 6 assembly may be used to introduce a first supercritical fluid through inner primary passage 51 and a solution/suspension of a substance of interest through outer primary passage 50. The mechanism in this case seems to involve the solution/suspension being formed into a thin conical "sheath" on the inner surface of the outer passage, around the outlet of inner passage 51. The surface of this sheath is destabilised by the high velocity supercritical fluid emerging from the inner passage; the sheath is broken into thin "ligaments" at the outlet of the outer passage 50 and is finally broken up, by the action of the two supercritical fluids, into separate fluid elements.

In the inlet assembly of FIG. 7, which is similar to that of FIG. 6, the inner primary passage 61 terminates downstream of the outlet end of outer primary passage 60. In this case, assuming the first supercritical fluid is introduced through outer primary nozzle passage 60 and the solution/suspension through inner primary passage 61 (as shown), both supercritical fluid flows would serve to disperse the solution or suspension and extract the vehicle from it. As in the nozzle of FIG. 6, particles formed when the fluids come into contact with one another are directed away via the intermediate chamber 63.

Shown in dotted lines in FIG. 7 is an inner secondary nozzle passage 64, through which another fluid could be introduced into the system if required. Generally, the primary nozzle may comprise two or more passages; the secondary nozzle may at the same time comprise one or more concentric passages.

Again, as for FIG. 6, the FIG. 7 assembly could equally well be used to introduce supercritical fluids through the inner nozzle passages and solution/suspension through the outer.

The FIG. 8 and FIG. 9 assemblies allow the introduction of a target solution or suspension in a direction roughly perpendicular to that of two counter-current supercritical fluid flows. In FIG. 8, the assembly comprises two oppositely directed single-passage nozzles 70 and 72, through which supercritical fluid will typically be introduced, an intermediate chamber 73 and a third nozzle 75 through which a solution or suspension of a substance of interest can be introduced directly into the supercritical fluid streams.

A modified version of the FIG. 8 apparatus (see FIG. 9) includes an additional primary nozzle passage 71, allowing the introduction of another solution or suspension with one of the supercritical fluid flows. Both solution/suspension flows (ie, that through nozzle passage 75 and that through passage 71) are dispersed by the supercritical fluids flowing through passages 70 and 72. The provision of two solution/suspension inlets means that the assembly of FIG. 9 may be used for a whole range of different processes, such as in situ reactions and the like.

Experimental Examples

The following experiments were carried out using apparatus of the type illustrated in FIGS. 1–5. A method in accordance with the invention was used to generate particles of the substances of interest, in a highly controlled manner.

Where fluid flow rates are quoted, these are as measured at the relevant fluid pump heads. In the case of supercritical fluid flows, the pump flow rates were for the liquid, prior to its passage through a heat exchanger to o take it into the supercritical state.

EXAMPLE 1

In this experiment, nicotinic acid particles were generated from a solution of nicotinic acid in absolute ethanol, used, but with the fluid inlet assembly of FIG. 2 replaced by a simple two-passage concentric inlet nozzle of the type illustrated in WO-95/01221 and WO-96/00610, the nicotinic acid solution being introduced through the inner of the two passages and the supercritical $CO_2$ through the outer.

Particle size data were recorded for both processes and compared, in order to demonstrate the improved results obtainable using the method of the present invention.

Experimental Conditions

In both experiments, the conditions inside the particle formation vessel were 90 bar and 90° C. A 0.625% w/v solution of nicotinic acid in absolute ethanol was fed to the relevant inlet assembly at a flow rate of 0.3 ml/min. The flow rate of the supercritical $CO_2$ into the inlet assembly was 9 ml/min—in the case of the "cross-flow" inlet assembly of the present invention, this gave two opposing $Co_2$ flows each at a rate of 9 ml/min.

Figure 5:
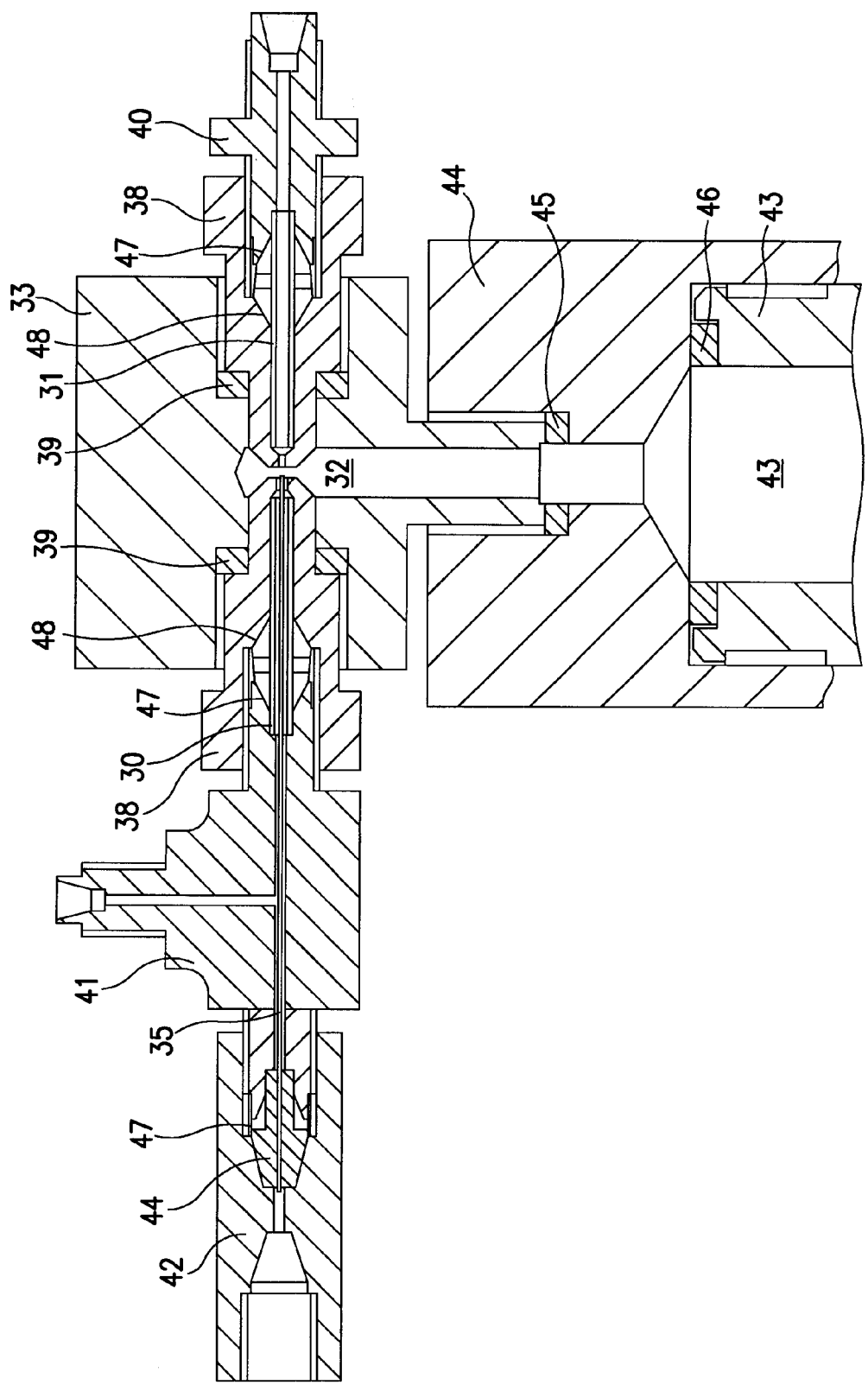

The nicotinic acid particles were collected in the particle collection vessel, ie, the Keystone high pressure vessel labelled 43 in FIG. 5.

For the control experiment, particle sizes were measured by aerodynamic diameter using the Aerosizer/Aerodisperser (Amherst Processing Instruments) dry powder analyser. For the particles prepared according to the invention, particle sizes were determined by suspension in ether and analysis using the Malvern LoC PCS system.

Each experiment was run twice.

Results

The results of the particle size analyses are summarised in the table below.

Particle Size Analysis

| Type of Nozzle | | Median particle diameter (nm) | Particle diameter by number: 90% diameter (nm) |
|---|---|---|---|
| Two component[1] concentric nozzle (control) | Run 1 | 3276 | 6567 |
| | Run 2 | 3112 | 6154 |
| Cross flow[2] nozzle | Run 1 | 400 | 1125 |
| | Run 2 | 750 | 2150 |

Figure 10:
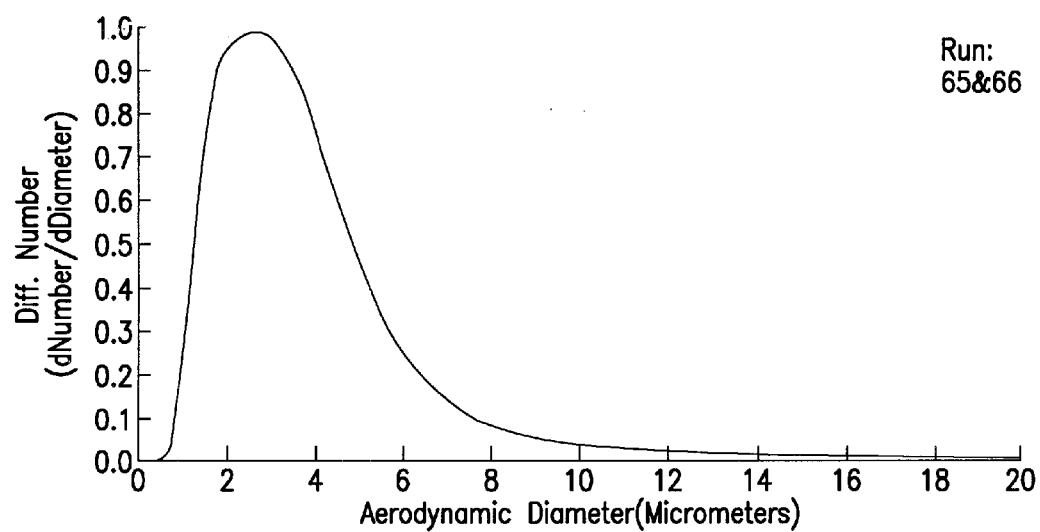

[1]Size analysis method: Aerosizer/Aerodisperser dry powder analyser by aerodynamic diameter
[2]Size analysis method: suspension of particles in ether and analysis by Malvern LoC PCS The particle size distribution curves are shown in FIGS. 10 (control experiment) and 11 (cross-flow nozzle experiment, in accordance with the invention).

It can be seen that far smaller particles can be formed using the method of the invention than are possible using the prior art method, which itself tends to give superior results to other available techniques. Particles formed according to the invention had a median diameter significantly lower than could be achieved in the control experiment.

Figure 11:
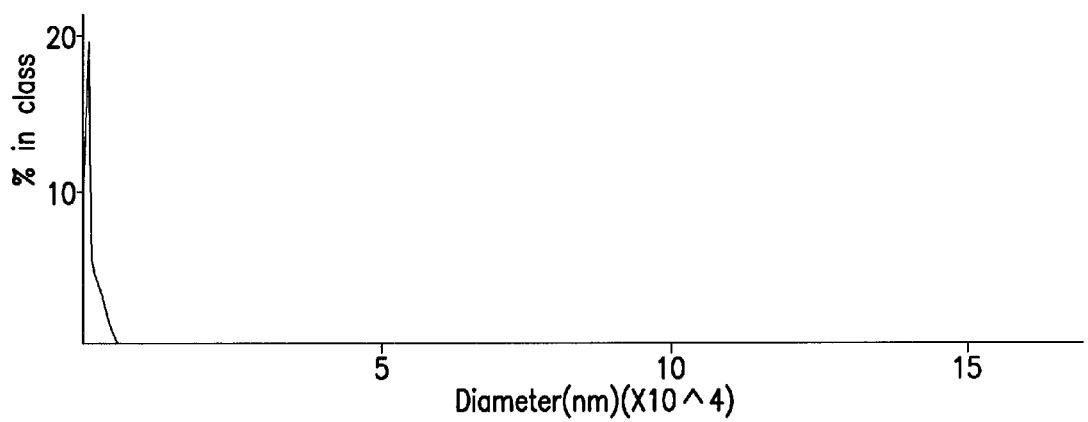

A well controlled particle size distribution was also achieved in both cases. The distribution achieved using the method of the present invention was particularly good, as can be seen from FIG. 11.

Figure 12A:
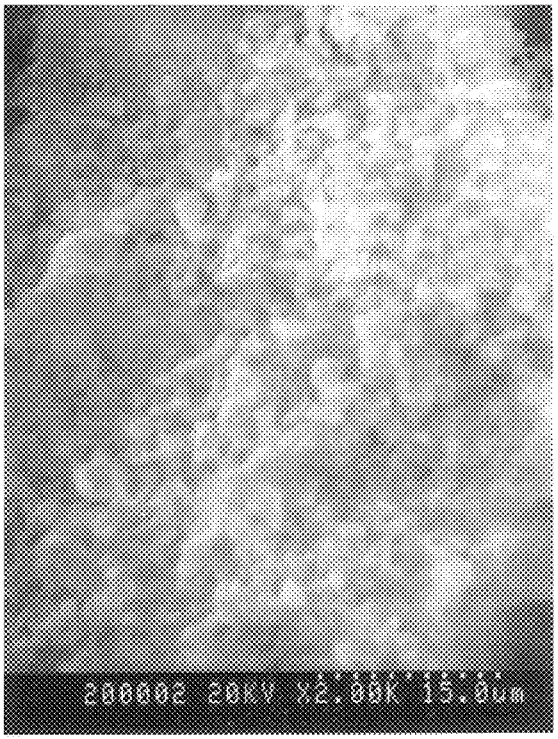
Figure 12B:
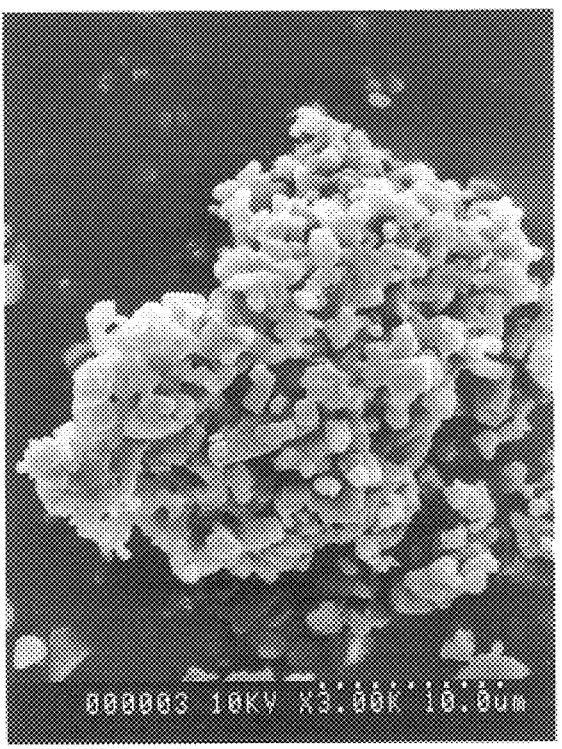

In both cases the particles formed were fine white crystalline powders. SEM micrographs of the products are shown in FIG. 12; FIG. 12A is the product of the cross flow nozzle experiment (Run 2); FIG. 12B the product of the control experiment (also Run 2).

EXAMPLE 2

Figure 7:
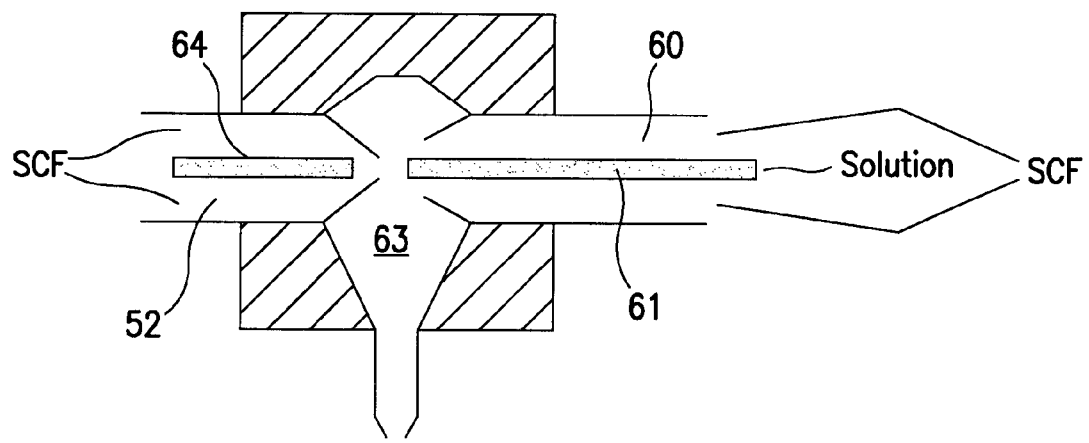
Figure 8:
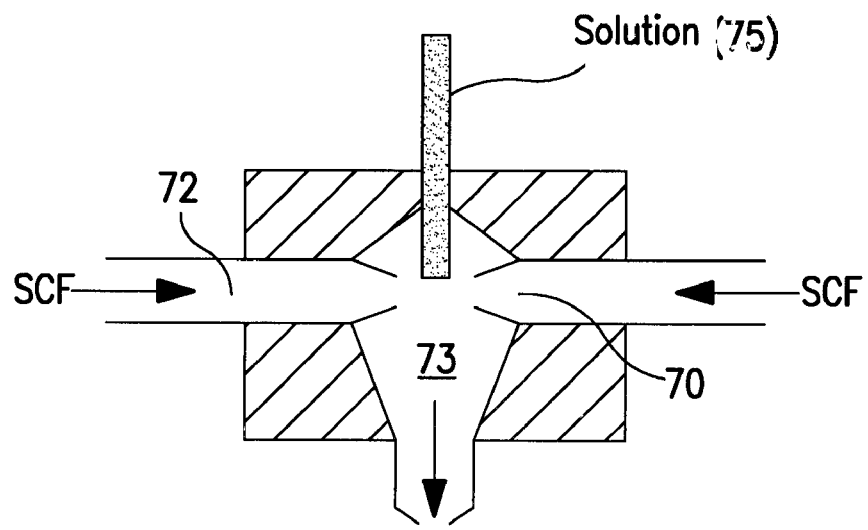
Figure 9:
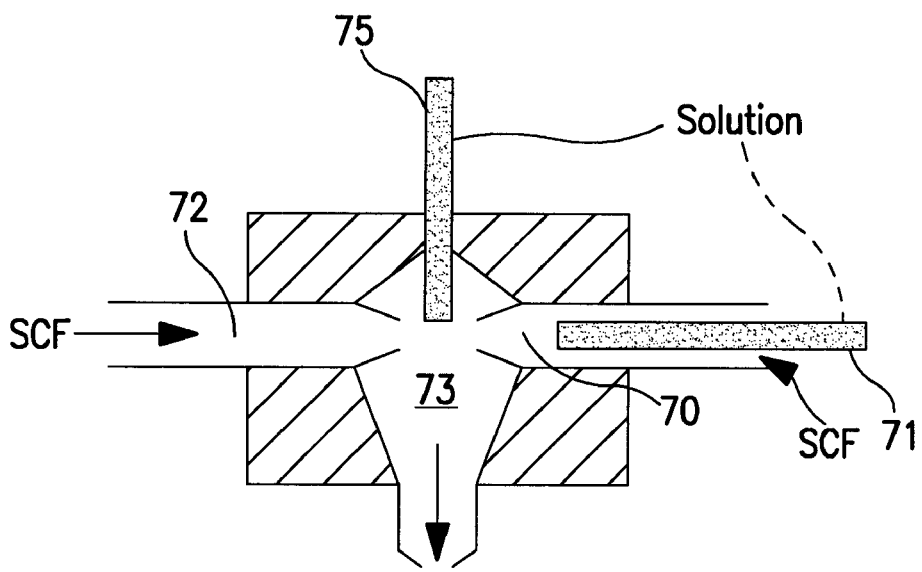

The apparatus of FIGS. 1–5 was used, ie, with a nozzle of the type shown in FIG. 7, having outer and inner primary passages 60 and 61 and a single secondary passage 62.

0.2 g of (α-[(t-Butylamino)methyl]-4-hydroxy-m-xylene-α,α-diol) (salbutamol, an asthma drug), from Sigma UK, lot 73F0007, was dissolved in 3 ml of methanol and 20 ml of acetone. This solution was introduced into the system (which was kept at 60° C. and 100 bar) with supercritical $CO_2$ flowing at 18 ml/min. The $CO_2$ was introduced through opposing passages 60 and 62 and the solution (0.1 ml/min) through inner passage 61.

At the end of experiment, a fine white free flowing powder was collected from the particle formation vessel (a 125 ml Keystone vessel) and stored free from light.

Figure 13:
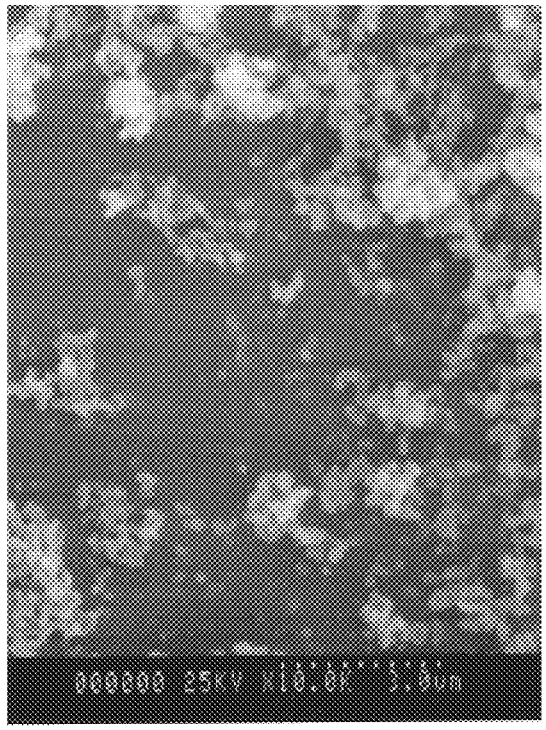

SEM micrographs revealed particles of rounded shape and mean diameter less than 500 nm (see FIG. 13).

EXAMPLE 3

Figure 6:
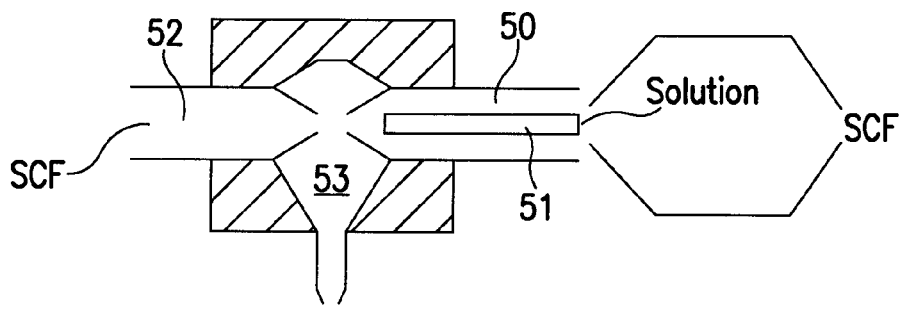

In the apparatus of FIGS. 1–5, a nozzle of the type shown in FIG. 6 was used, to allow a degree of internal mixing to occur between the SCF and the solution of interest, prior to dispersion by the two SCF flows. Nozzle passages 50 and 51 had internal diameters of 0.75 mm and 0.35 mm respectively; the wall of inner passage 51 had an external diameter of 0.65 mm. The outlet of passage 50 was of diameter 0.15 mm. The gap between the outlets of the two outer passages 50 and 52, in the intermediate chamber 53, was 0.15 mm.

Figure 14:
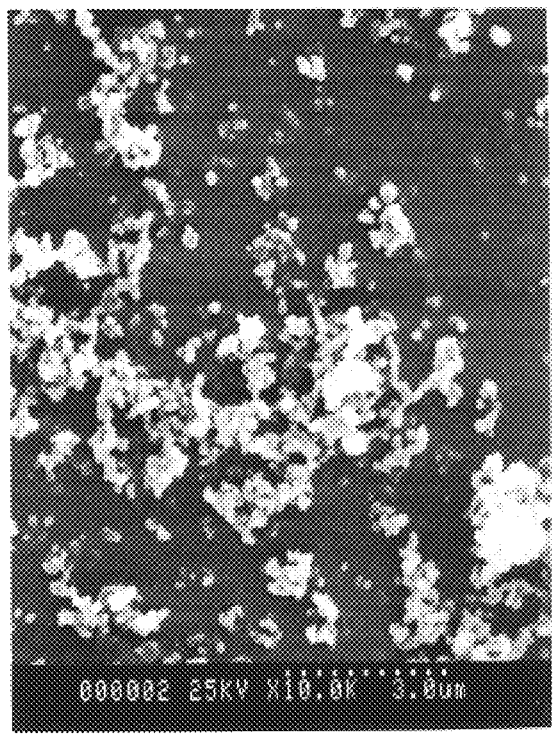

0.2 g of salbutamol was dissolved in 3 ml of methanol and 20 ml of acetone prior to introduction to the particle formation vessel (a 125 ml Keystone vessel) kept at 100 bar and 60° C. Supercritical $CO_2$ flowed at 18 ml/min through passages 51 and 52, and the solution flow through passage 50 was kept at 0.2 ml/min. A fine, white, free flowing powder was collected at the end of the experiment and stored in amber bottles. SEM analysis revealed spherical particles with a mean diameter below 500 nm (FIG. 14).

EXAMPLE 4

This experiment was used to produce silver nitrate particles having well controlled physicochemical characteristics.

Emulsions of microparticles of silver salts are often used to coat films and paper in the photographic industry. Picture resolution and film speed are affected by the size of particles of the salts present in the emulsion. The finer the particle size, the higher the resolution and the slower the speed of the final product (film or print). Therefore, a substantial amount of effort has been directed in the past to producing a high resolution product with a high film speed. It would be highly desirable if the SEDS process could be used to prepare very fine, monodisperse particles of an inorganic photo-sensitive material.

In this experiment, a solution of 2% w/v silver nitrate in methanol was pumped at 0.1 ml/min into the 125 ml Keystone vessel kept at 100 bar and 70° C. The nozzle used was that of Example 3. Supercritical $CO_2$, flowing at 18 ml/min, was introduced through passages 51 and 52, the solution through passage 50.

Figure 15:
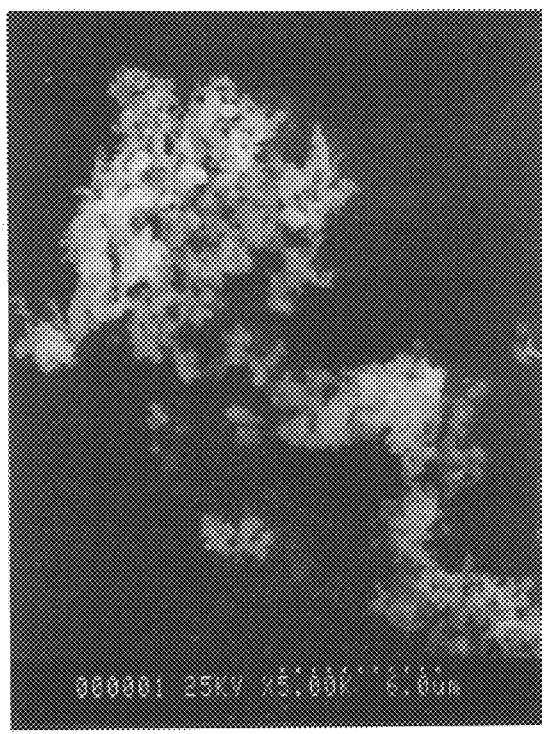

A fine, off-white, free flowing powder was collected at the end of the experiment and stored free from light. SEM photomicrographs showed spherical habit nanoparticles (mean diameter around 300 nm) with a very uniform size distribution (FIG. 15).

Figure 16:
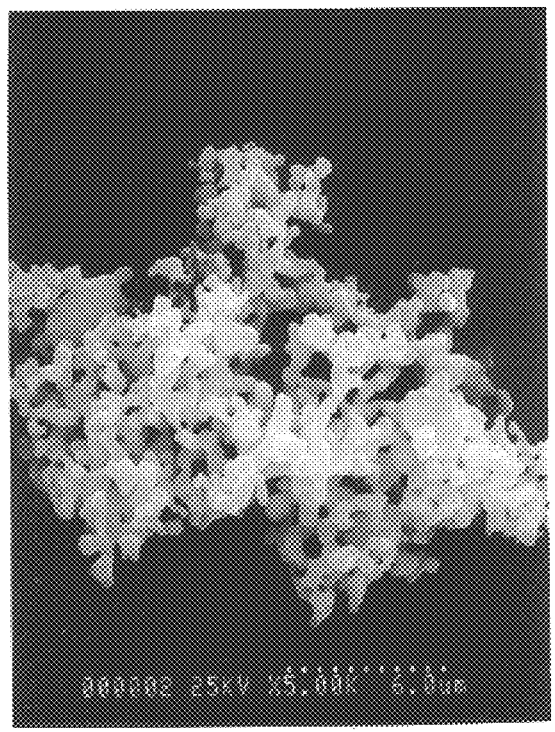

To study the effects of the working conditions on the particle size of the products, the pressure was raised from 100 to 150 bar and the temperature was lowered from 70 to 50° C. The nozzle configuration, fluid flow rates and solution concentration remained constant The product, a fine free flowing powder, when examined under the SEM showed an increase in mean particle diameter from around 300 nm to around 1000 nm (FIG. 16). It could be that the increase of the density of the supercritical $CO_2$ from 0.25 $g/cm^3$ (100 bar, 70° C.) to 0.71 $g/cm^3$ (150 bar, 50° C.) led to a reduction in its linear velocity and hence in the degree of dispersion of the solution. However, we do not wish to be bound by this explanation.

EXAMPLE 5

Using the apparatus of Example 2, a 0.2% w/v solution of polystyrene in toluene was introduced through inner passage 61 at 0.2 ml/min. Supercritical $CO_2$ was introduced at 18 ml/min through passages 60 and 62. The particle formation vessel (Keystone, 125 ml) was kept at 100 bar and 35° C.

Figure 17:
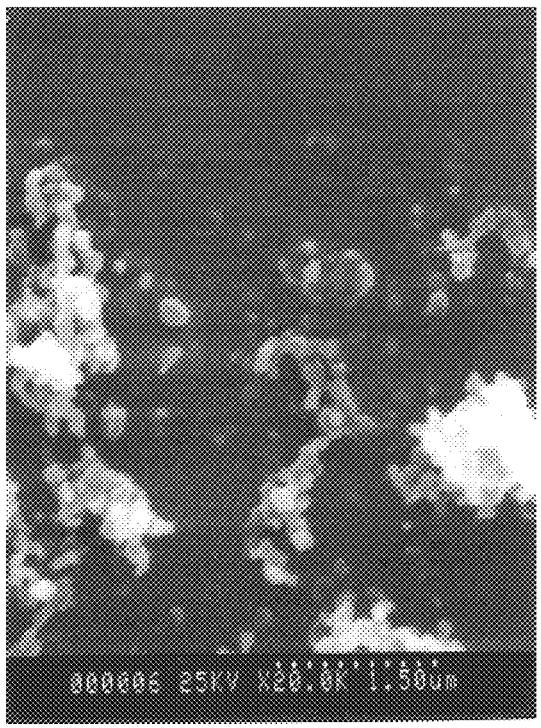

At the end of the experiment a fine white powder was collected and stored in a screw-cap bottle. SEM photomicrographs showed very uniform spherical particles of mean diameter about 300 nm (FIG. 17).

EXAMPLE 6

In this experiment, a polystyrene solution was introduced into the apparatus of Example 3. The solution concentration was 0.2% w/v in toluene and it was introduced with a flow rate of 0.2 ml/min through passage 50. Supercritical $CO_2$ (flow rate 18 ml/min) was introduced into the particle formation vessel (125 ml, Keystone), kept at 150 bar and 35° C., through nozzle passages 51 and 52.

The product, a fine, fluffy, free flowing white powder, was collected at the end of the experiment and stored in a screw-cap bottle.

Figure 18:
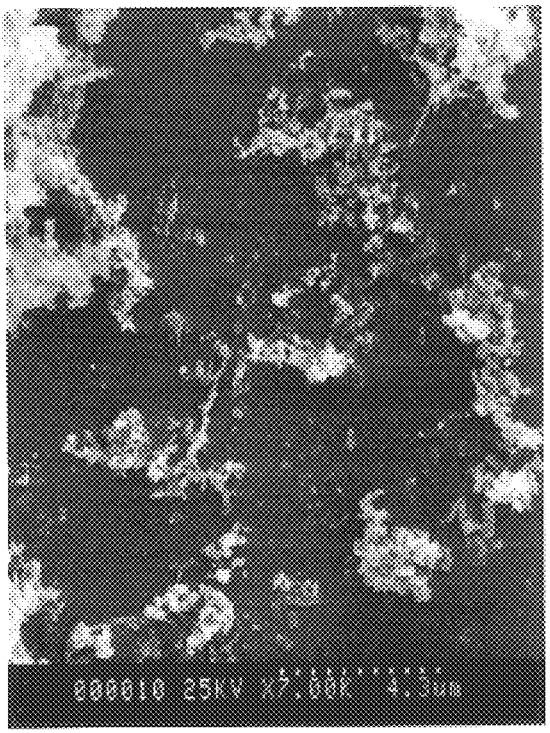

The mean particle diameter of the product was around 500 nm when examined by the SEM (FIG. 18).

The above examples demonstrate the effective use of the method and apparatus of the invention to produce a variety of products, both organic and inorganic, monomers and polymers. In each case the products have highly desirable particle characteristics.

EXAMPLE 7

Samarium is a rare earth metal used in the manufacture of soft permanent magnets for electronic devices, and also in ceramic products. In this experiment, particles of its acetate were produced.

0.2 g of samarium acetate was dissolved in 2 ml of deionised water and 20 ml of methanol and introduced into the apparatus of Example 3, at a flow rate of 0.2 ml/min. Two opposing flows of supercritical $CO_2$, each at 18 ml/min, were introduced through the nozzle as well. The pressure and temperature in the 125 ml Keystone vessel were maintained at 150 bar and 50° C. respectively. At the end of the experiment the product, a fine fluffy white powder, was collected and stored free from moisture.

Figure 19:
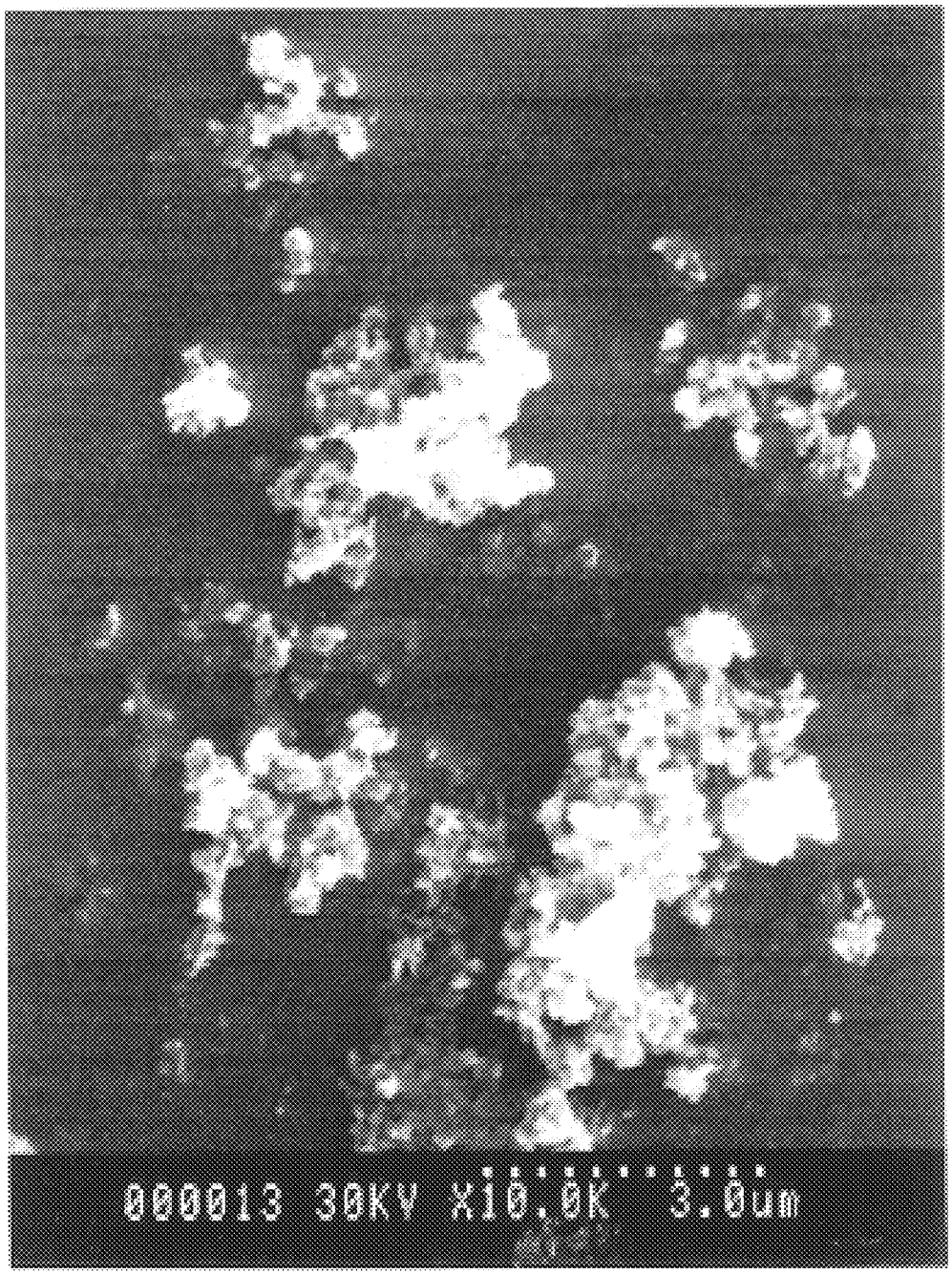

SEM photomicrographs of the product (see FIG. 19) revealed loose aggregates with a rounded shape, the mean diameter of individual particles being around 200 nm.

What is claimed is:

1. A method for forming particles of a substance, the method comprising: (a) introducing into a particle formation chamber, the temperature and pressure in which are controlled, a first supercritical fluid and a solution or suspension of the substance in a vehicle; (b) simultaneously introducing, into the particle formation chamber, an impinging flow of a second supercritical fluid, at an angle to, and directed at, the direction of flow of the first supercritical fluid, the first and second supercritical fluids entering the particle formation chamber separately; and (c) using either or both of the first and second supercritical fluids to disperse the solution or suspension, and to extract the vehicle from it, substantially simultaneously and substantially immediately on introduction of the fluids into the particle formation chamber.

2. A method of claim 1 wherein the first and second supercritical fluids are different.

3. A method according to claim 1, wherein the directions of flow of the first supercritical fluid and the solution or suspension are substantially parallel.

4. A method according to claim 3, wherein the directions of flow of the first supercritical fluid and the solution or suspension are coaxial.

5. A method according to claim 1, wherein the solution or suspension is introduced at an angle to the flow of the first supercritical fluid.

6. A method according to claim 1, wherein the first and second supercritical fluids are the same.

7. A method according to claim 1, wherein the ratio of the solution/suspension flow rate to each supercritical fluid flow rate is between 0.001 and 0.2.

8. A method according to claim 1, additionally involving collecting the particles, following their formation, in the particle formation chamber.

9. A method according to claim 1, which is carried out in a substantially continuous manner.

10. A method of claim 1 wherein the flow rates of the first and second supercritical fluids are greater than that of the target solution or suspension.

11. A method of claim 10 wherein the ratio of the solution or suspension flow rate to each supercritical fluid flow rate is between 0.001 and 0.2.

12. A method of claim 1 wherein the solution or suspension is introduced in a direction perpendicular to the flow of the first supercritical fluid.

13. A method for forming particles of a substance, the method comprising: (a) introducing into a particle formation chamber, the temperature and pressure in which are controlled, a first supercritical fluid and a solution or suspension of the substance in a vehicle; (b) simultaneously introducing, into the particle formation chamber, an impinging flow of a second supercritical fluid, at an angle to, and directed at, the direction of flow of the first supercritical fluid; and (c) using either or both of the first and second supercritical fluids to disperse the solution or suspension, and to extract the vehicle from it, substantially simultaneously and substantially immediately on introduction of the fluids into the particle formation chamber, wherein the first and second supercritical fluid flows are directed at one another in substantially opposite directions.

14. Apparatus for use in a method of forming particles of a substance, comprising a particle formation chamber; a mechanism for controlling the temperature in the chamber at a desired level; a mechanism for controlling the pressure in the chamber at a desired level; a first fluid inlet for the separate introduction into the chamber of (i) a first supercritical fluid and (ii) a solution or suspension of the substance in a vehicle; a pump for conveying the solution or suspension to the first fluid inlet; and a second fluid inlet for introducing simultaneously an impinging flow of a second supercritical fluid into the particle formation chamber separately from the first supercritical fluid, at an angle to, and directed at, the direction of flow of the first supercritical fluid, the apparatus being such as to allow dispersion of the solution or suspension, and extraction of the vehicle, to occur substantially simultaneously and substantially immediately on introduction of the fluids into the particle formation chamber, by the action of either or both of the two supercritical fluids.

15. Apparatus according to claim 14, wherein the first fluid inlet allows the co-introduction of the first supercritical fluid and the solution or suspension in substantially parallel directions.

16. Apparatus according to claim 15, wherein the first fluid inlet allows the co-introduction of the first supercritical fluid and the solution or suspension coaxially.

17. Apparatus according to claim 14, wherein the first and second fluid inlets comprise first and second nozzles respectively.

18. Apparatus according to claim 14, wherein the first fluid inlet comprises two nozzles, one for introduction of the first supercritical fluid and one for introduction of the solution or suspension, arranged at an appropriate angle relative to one another.

19. Apparatus according to claim 14, wherein the first and second fluid inlets both form part of a single fluid inlet assembly usable to introduce all fluids into the particle formation chamber.

20. Apparatus according to claim 19, wherein the fluid inlet assembly comprises:
   a) a primary nozzle having two or more concentric passages, through which may be introduced a flow of the first supercritical fluid and a flow of the solution or suspension; and
   b) a secondary nozzle having at least one passage directed at an angle to the primary nozzle passages, trough which secondary nozzle passage a flow of the second supercritical fluid may be introduced; and
   c) a third nozzle having at least one passage directed perpendicularly to the at least one passage of the primary nozzle, through which third nozzle passage a flow of the solution or suspension may be introduced,
   the outlets of the primary, secondary, and third nozzle passages being positioned so as to allow supercritical fluid flowing through the secondary nozzle to impinge upon supercritical fluid flowing through the primary nozzle and solution or suspension flowing through the third nozzle.

21. Apparatus according to claim 19, wherein the fluid inlet assembly comprises:
   a) a primary nozzle having two or more concentric passages, through which may be introduced a flow of the first supercritical fluid and a flow of the solution or suspension; and
   b) a secondary nozzle having at least one passage directed at an angle to the primary nozzle passages, through which secondary nozzle passage a flow of the second supercritical fluid may be introduced,
   the outlets of the primary and secondary nozzle passages being positioned so as to allow supercritical fluid flowing through the secondary nozzle to impinge upon supercritical fluid flowing through the primary nozzle.

22. Apparatus according to claim 21, wherein the secondary nozzle passage is coaxial with the primary nozzle passages but points in the opposite direction, so that the outlet end of the secondary nozzle passage faces the outlet ends of the primary nozzle passages.

23. Apparatus according to claim 21, wherein the primary nozzle passages are of the type which allow prefilming of at least one of the fluids to occur, immediately prior to its contact with the other fluids.

24. Apparatus according to claim 21, wherein the outlet of an inner passage of the primary nozzle occurs either upstream or downstream of that of one or more of the surrounding outer passage(s).

25. Apparatus according to claim 24 wherein the inner passage terminates upstream of that of one or more of the surrounding passage(s).

26. Apparatus according to claim 21, wherein the secondary nozzle comprises two or more concentric passages.

27. Apparatus according to claim 26, wherein the secondary nozzle passages are of the type which allow pre-filming of at least one of the fluids to occur, immediately prior to its contact with the other fluids.

28. Apparatus according to claim 21, wherein the fluid inlet assembly comprises an intermediate chamber located between the primary and the secondary nozzle outlets, in which chamber the fluids may meet and interact.

29. Apparatus according to claim 28, wherein the intermediate chamber is shaped to direct the fluids and/or particles formed from them, away from the point at which the fluids meet.

30. Apparatus according to claim 28, wherein the intermediate chamber is directed roughly perpendicular to the primary and secondary nozzle passages, and in use is downwardly directed so as to allow gravity to contribute to removal of particulate products from the nozzle outlet region.

31. Apparatus according to claim 14, wherein the first fluid inlet is such as to allow dispersion of the solution or suspension, and extraction of the vehicle, to occur substantially simultaneously and substantially immediately on introduction of the first supercritical fluid into the particle formation chamber, by the action of at least the first supercritical fluid.

32. Apparatus according to claim 18 wherein the two nozzles allow the solution or suspension to be introduced in a direction perpendicular to the direction of flow of the first supercritical fluid.

33. Apparatus for use in a method of forming particles of a substance, comprising a particle formation chamber; a mechanism for controlling the temperature in the chamber at a desired level; a mechanism for controlling the pressure in the chamber at a desired level; a first fluid inlet for the introduction into the chamber of a first supercritical fluid and a solution or suspension of the substance in a vehicle; and a second fluid inlet for introducing simultaneously an impinging flow of a second supercritical fluid, at an angle to, and directed at, the direction of flow of the first supercritical fluid, the apparatus being such as to allow dispersion of the solution or suspension, and extraction of the vehicle, to occur substantially simultaneously and substantially immediately on introduction of the fluids into the particle formation chamber, by the action of either or both of the two supercritical fluids, wherein the second fluid inlet allows the introduction of the second supercritical fluid in a direction substantially opposite to the direction of flow of the first supercritical fluid.

* * * * *